(12) United States Patent
Waizenegger et al.

(10) Patent No.: US 11,071,571 B2
(45) Date of Patent: Jul. 27, 2021

(54) IMPLANT FOR REINFORCING A BONE, COMPRISING A BORE VECTOR SPECIFYING HOLE AND SURROUNDING PLATE FOR A JAW REPLACEMENT, AND IMPLANT PRODUCTION METHOD

(71) Applicant: Karl Leibinger Medizintechnik GmbH & Co. KG, Mühlheim (DE)

(72) Inventors: Axel Waizenegger, Mühlheim (DE); Frank Reinauer, Mühlheim (DE); Nils-Claudius Gellrich, Mühlheim (DE); Majeed Rana, Mühlheim (DE)

(73) Assignee: Karl Leibinger Medizintechnik GmbH & Co. KG, Mühlheim (DE)

( * ) Notice: Subject to any disclaimer, the term of this patent is extended or adjusted under 35 U.S.C. 154(b) by 359 days.

(21) Appl. No.: 16/062,830

(22) PCT Filed: Dec. 16, 2016

(86) PCT No.: PCT/EP2016/081535
§ 371 (c)(1),
(2) Date: Jun. 15, 2018

(87) PCT Pub. No.: WO2017/108627
PCT Pub. Date: Jun. 29, 2017

(65) Prior Publication Data
US 2020/0281635 A1    Sep. 10, 2020

(30) Foreign Application Priority Data

Dec. 23, 2015 (DE) .................. 10 2015 122 793.2

(51) Int. Cl.
*A61B 17/80* (2006.01)
*A61B 34/10* (2016.01)
(Continued)

(52) U.S. Cl.
CPC ........ *A61B 17/8071* (2013.01); *A61B 17/176* (2013.01); *A61B 34/10* (2016.02);
(Continued)

(58) Field of Classification Search
CPC . A61B 17/80; A61B 17/8252; A61B 17/8057; A61B 17/8061; A61B 17/78071; A61B 17/8085; A61F 2/2803
See application file for complete search history.

(56) References Cited

U.S. PATENT DOCUMENTS

| 4,364,382 A | 12/1982 | Mennen |
| 4,726,808 A * | 2/1988 | Collins ................. A61F 2/2803 623/17.17 |

(Continued)

FOREIGN PATENT DOCUMENTS

| CN | 101883532 A | 11/2010 |
| CN | 102858257 A | 1/2013 |

(Continued)

OTHER PUBLICATIONS

Apr. 21, 2020 (RU) English Translation of Office Action and Search Report—Application No. 2018126465/14 (041963).
(Continued)

*Primary Examiner* — Eric S Gibson
(74) *Attorney, Agent, or Firm* — Banner & Witcoff, Ltd.

(57) ABSTRACT

The invention relates to an implant for attaching to a bone, having bone support surfaces or bone formfitting sections which are inclined relative to each other in order to rest on the surface of the bone. Two bone formfitting sections are aligned relative to each other in a sub-region of the implant such that surrounding the bone in the sub-region secures the position of the implant. The invention also relates to a method for producing an implant according to the invention.

9 Claims, 4 Drawing Sheets

(51) Int. Cl.
*A61B 17/17* (2006.01)
*A61B 17/00* (2006.01)

(52) U.S. Cl.
CPC ........... *A61B 2017/00526* (2013.01); *A61B 2034/102* (2016.02); *A61B 2034/108* (2016.02)

(56) References Cited

U.S. PATENT DOCUMENTS

| | | | | |
|---|---|---|---|---|
| 5,769,637 | A * | 6/1998 | Morgan | A61C 8/0006 433/176 |
| 6,325,803 | B1 * | 12/2001 | Schumacher | A61B 17/8047 606/104 |
| 6,350,265 | B1 * | 2/2002 | Blaustein | A61B 17/8071 606/300 |
| 6,423,068 | B1 * | 7/2002 | Reisberg | A61B 17/8071 606/280 |
| 7,887,587 | B2 * | 2/2011 | Griffiths | A61L 27/54 623/16.11 |
| 8,911,443 | B2 | 12/2014 | Graham et al. | |
| 8,945,220 | B2 * | 2/2015 | Griffiths | A61F 2/2803 623/16.11 |
| 9,411,939 | B2 * | 8/2016 | Furrer | A61B 17/8071 |
| 10,192,002 | B2 * | 1/2019 | Benker | G06F 30/00 |
| 10,548,668 | B2 * | 2/2020 | Furrer | A61B 17/8071 |
| 10,595,942 | B2 * | 3/2020 | Rueber | G06T 19/20 |
| 10,610,299 | B2 * | 4/2020 | Rueber | G06F 30/00 |
| 2005/0273165 | A1 * | 12/2005 | Griffiths | A61L 27/54 623/16.11 |
| 2006/0212158 | A1 * | 9/2006 | Miller | A61C 13/0004 700/163 |
| 2010/0106197 | A1 * | 4/2010 | Buscher | A61B 17/151 606/286 |
| 2011/0098760 | A1 * | 4/2011 | Griffiths | A61L 27/16 606/86 R |
| 2011/0144698 | A1 * | 6/2011 | Buchbinder | A61B 17/8071 606/280 |
| 2011/0184414 | A1 * | 7/2011 | Andermahr | A61B 17/809 606/70 |
| 2011/0269100 | A1 * | 11/2011 | Furrer | A61B 17/1739 433/72 |
| 2011/0301609 | A1 * | 12/2011 | Longepied | A61B 17/8085 606/71 |
| 2011/0306976 | A1 | 12/2011 | Kubiak et al. | |
| 2012/0029574 | A1 * | 2/2012 | Furrer | A61B 17/151 606/280 |
| 2012/0150243 | A9 * | 6/2012 | Crawford | G16H 50/50 606/86 R |
| 2012/0285002 | A1 * | 11/2012 | Lin | A61B 17/80 29/592 |
| 2014/0074438 | A1 * | 3/2014 | Furrer | A61B 17/8071 703/1 |
| 2014/0128923 | A1 | 5/2014 | Ellis et al. | |
| 2014/0172021 | A1 | 6/2014 | Castaneda et al. | |
| 2014/0277174 | A1 * | 9/2014 | Cornelius | A61B 17/8085 606/281 |
| 2015/0051876 | A1 * | 2/2015 | Rueber | A61B 34/10 703/1 |
| 2015/0209093 | A1 | 7/2015 | Dallis | |
| 2015/0272598 | A1 * | 10/2015 | Dubois | A61B 17/1673 606/280 |
| 2016/0296290 | A1 * | 10/2016 | Furrer | A61B 34/10 |
| 2016/0331427 | A1 * | 11/2016 | Waizenegger | A61B 17/8071 |
| 2017/0014169 | A1 * | 1/2017 | Dean | A61B 17/8071 |
| 2017/0216033 | A1 * | 8/2017 | Daniel | A61F 2/2803 |
| 2017/0238981 | A1 * | 8/2017 | Madjarov | A61B 17/8085 |
| 2017/0296242 | A9 * | 10/2017 | Waizenegger | A61B 17/8071 |
| 2017/0348023 | A1 * | 12/2017 | Thiel | A61B 17/8645 |
| 2017/0360453 | A1 * | 12/2017 | Brailovski | A61B 17/15 |
| 2018/0103965 | A1 * | 4/2018 | Waizenegger | A61B 17/1728 |
| 2018/0103990 | A1 * | 4/2018 | Thiel | A61B 17/8665 |
| 2019/0070005 | A1 * | 3/2019 | Brailovski | A61B 17/1728 |
| 2019/0070006 | A1 * | 3/2019 | Goh | A61F 2/4601 |
| 2019/0357952 | A1 * | 11/2019 | Waizenegger | A61B 17/8071 |
| 2020/0179052 | A1 * | 6/2020 | Rueber | G06F 30/00 |
| 2020/0205984 | A1 * | 7/2020 | Lee | B33Y 50/00 |

FOREIGN PATENT DOCUMENTS

| | | |
|---|---|---|
| DE | 299 09 616 U1 | 11/1999 |
| DE | 10 2008 051 532 A1 | 4/2010 |
| DE | 102008058305 A1 | 5/2010 |
| DE | 10 2013 102 178 A1 | 7/2014 |
| EP | 2838458 A1 | 2/2015 |
| EP | 2698122 B1 | 7/2017 |
| RU | 2092125 C1 | 10/1997 |
| RU | 2238055 C1 | 10/2004 |
| WO | 2011/136775 A1 | 11/2011 |
| WO | 2013156545 A1 | 10/2013 |
| WO | 20141188036 A1 | 11/2014 |
| WO | 2015/155296 A1 | 10/2015 |

OTHER PUBLICATIONS

Apr. 21, 2020 (RU) Russian Office Action and Search Report—Application No. 2018126465/14 (041963).

Mar. 28, 2017—PCT/EP2016/081535 ISR and WO.

Aug. 13, 2020 (RU) English translation of Examination Report—Application No. 2018126465 14 041963.

Aug. 13, 2020 (RU) Russian Examination Report—Appllication No. 2018126465 14 041963.

Jul. 27, 2020 (CN) Chinese Office Action—Application No. 201680076048.8.

Jul. 27, 2020 (CN) English translation of First Office Action—Application No. 201680076048.8.

* cited by examiner

IMPLANT FOR REINFORCING A BONE, COMPRISING A BORE VECTOR SPECIFYING HOLE AND SURROUNDING PLATE FOR A JAW REPLACEMENT, AND IMPLANT PRODUCTION METHOD

CROSS-REFERENCE TO RELATED APPLICATIONS

This application is a U.S. National Stage application under 35 U.S.C. § 371 of International Application PCT/EP2016/081535 (published as WO 2017/108627 A1), filed Dec. 16, 2016, which claims the benefit of priority to Application DE 10 2015 122 793.2, filed Dec. 23, 2015. Benefit of the filing date of each of these prior applications is hereby claimed. Each of these prior applications is hereby incorporated by reference in its entirety.

The present invention relates to an implant for attaching to a bone, for example of a mammal such as a primate, e.g. a human being, having bone support surfaces or bone formfitting sections which are inclined relative to each other in order to rest on the surface of a bone, and a method for producing an implant.

From the state of the art implants for trauma and reconstruction surgery are known which are in the form of custom-made plates. The latter are produced by way of computer tomography data (CT data) tailored to the patient. In this way, the design of said plate can be adapted to the individual anatomic conditions of the patient.

Thus, for example DE 10 2013 102 178 A1 discloses a sternum osteosynthesis system in the form of a clip having a first leg, a second leg and a connecting area.

DE 10 2008 051 532 A1 discloses a method for preoperative adaptation of an implant serving for fixing the fracture fragments of a bone to the outer contour of the bone. Accordingly, a digital model of the implant in a non-bent state is shown along with a digitalized X-ray showing the bone with reduced fracture fragments on a screen and is virtually bent so as to adapt the same to the outer contour of the shown bone. The virtual model adapted in this way then serves as a template for bending the implant.

US 2014/0128923 A1 discloses a system including a method, a device and equipment for fixing bones by bone plates. A similar implant is known from US 2015/0209093 A1.

U.S. Pat. No. 4,364,382 A discloses a fixing device for bone fractures which can do without any screws and is secured in its position by bending and penetrating the bone and in this way fixes the fracture point.

Furthermore, from DE 299 09 616 U1 an example of a conventional boring device is known.

Such implant is plate-shaped, wherein the plate abuts on a bone surface. For fastening the implant to the bone, plural through-bores which can be individually secured in their (spatial) position and their bending/geometry in surgical use, viz. during operation are provided on the plate. The screw hole arrangement can be determined according to the individual anatomic structures such as e.g. roots or nerves, or according to already existing or intended implants. Such individual design has also been necessary on the spot so far in order to avoid damage to the patient such as damage of nerves.

However, the screw position during surgical use can be varied only in a spatial plane within an angular range of from 0° to a maximum of 15°, wherein this spatial plane is aligned perpendicularly to the plate surface. In this way, the selection of the screw positions for securing the implant to the bone is extremely restricted. Moreover, the previous implants usually have been beam-shaped, this means that the implant has a large length as compared to its cross-section. The width/height of the implant equally restricts the positioning of the screws. Also, such conventional implants are esthetically not appealing and show certain medical drawbacks.

Moreover, for attaching this implant to the bone a boring template with drill guide bushes aligned with the plate holes contained in the conventional plate has been necessary so far to introduce the bores into the bone according to the design.

By abutting the plate on a bone surface, a quasi or almost parallel alignment of the implant along the bone is formed. Since the implant is in the form of a plate, the boreholes for introducing the screws can be formed exclusively on the front surface (surface in parallel to the bone support surface), however. In this way, the positioning of the screws is restricted to the fact that they can be provided exclusively from the front, this means exactly from this front surface. This restricts the introducing capability, on the one hand, but also the quality of the connection, on the other hand.

It is now the object of the invention to eliminate or at least alleviate the drawbacks known from the state of the art.

This object is achieved according to the invention in a generic device by the fact that in a sub-region of the implant inserted in its original shape two bone formfitting sections are aligned with each other so that there surrounding of the bone (forcedly) secures the position of the implant abutting on the bone in all three spatial directions unambiguously, i.e. relative to the bone and in space.

Advantageous embodiments are claimed in the subclaims and shall be explained as follows.

It is advantageous when the implant includes screw holes which are aligned such that they are provided/can be used as boring template for introducing bores into the bone. Thus, the implant at the same time serves as a boring template, which is why the operating surgeon no longer has to position any separate boring template. This helps to considerably facilitate the realization of the bores in the bone which serve for receiving e.g. screws. Gentler treatment of the patient with even less expenditure of time becomes possible.

It is advantageous when the screw holes are aligned at least diagonally/transversely or skew relative to each other or to a longitudinal axis of the implant. A diagonal alignment of the screw holes in this context means that the screws in a spatial direction are not arranged in parallel to each other, and skew describes the non-parallel alignment of the screw holes in at least two spatial directions. Thus, the screws for securing the implant to the bone can be adapted individually to the respective patient and can be provided so that neither nerves nor teeth/roots are damaged.

An advantageous embodiment provides that the inner diameter of the screw hole is adjusted to the outer diameter of the drill and/or of the intended hole in the bone, for example free from play or forcedly aligned. In this way, the implant at the same time serves as a boring template.

It is advantageous when the inner diameter of the screw hole amounts to about 0.8, 0.85 or 0.9 to 0.99 times the intended bone hole. Within this range, especially precise positioning of the bone hole above the screw hole existing in the implant is possible.

Another advantageous embodiment provides that the screw hole is arranged in the area of a support structure of the implant.

Accordingly, it is of advantage when the screw holes are configured to be tilted/diagonal relative to the surface of the support structure. Thus, the individual positioning of the screws according to the respective patient data is possible and at the same time a flux-optimized positioning of the screw holes can be provided.

It is moreover of advantage when the implant itself is configured and, resp., usable as a boring template including drill bushings/drill jig bushes. This allows to dispense with the use of a separate boring template, which facilitates the correct positioning and drilling of the bone holes during the surgical intervention for the operating surgeon.

Another advantageous embodiment provides that the support structure includes such outer contour, e.g. by extensions, prominences and/or recesses, which results in visible plastic modifications of the person to which the implant is implanted. In this way, plastic corrections and, resp., a reconstruction of originally existing contours can be carried out simultaneously with setting the implant.

Furthermore, a method for producing such implant is part of the invention.

For the method for producing such implant it is advantageous when, based on previously obtained patient-specific data, the screw seating holes are introduced to an implant base member so that after implanting the implant the screw seating holes are used as a forced guide for a drill which can be used for introducing holes into the bone.

Especially useful are modifications that are configured as follows:

A possible modification provides an implant for attaching to a bone, comprising a support structure which comprises at least one securing portion following the bone outer structure for being attached to the bone.

Accordingly, it is of advantage when a base is formed as an elevation or prominence standing out against the ambient outer contour of the support structure, such as in the form of a projection. Thus, further components may be secured to or in or above said base quickly and permanently at a predetermined position.

Moreover, it is of advantage when the base is an integral, single-piece and preferably single-material component of the support structure. The integral formation of the support structure and the base helps to avoid a junction and thus a potential weak point. This results in an especially stable implant.

Another aspect provides that the base is prepared for non-positively, positively and/or adhesively receiving the prosthesis or an intermediate part. This enables simple connection and, resp., mounting of the prosthesis or of the intermediate part.

An advantageous embodiment provides that the preparation is a thread such as a female or male thread or a retention shape, i.e. such contour which facilitates or enables positive and/or non-positive securing. The retention shape advantageously incorporates an undercut.

It is moreover advantageous when the retention shape includes a dome-shaped, ball-shaped or spherical distal part. The distal part enables simple attachment or simple connection to the prosthesis or the intermediate part.

It is further advantageous when the base has a snap-fit design. In this way, the prosthesis or the intermediate part can be easily clipped to the base and any further connecting elements such as e.g. screws can be dispensed with.

Another advantageous embodiment provides that the intermediate part is designed as a dental implant and holds, preferably while interposing an abutment, an artificial tooth or a crown or is prepared for holding or takes the shape of an abutment.

It is of advantage that the base extends along a direction transversely or diagonally to a longitudinal extension direction of the support structure. This enables the inclination of the base to correspond to the inclination of an artificial tooth/a crown secured thereto. Thus, adaptation of the artificial denture to the individual dentition structure of the patient—and hence also flux-optimized positioning of the prosthesis-implant combination—is possible.

Moreover, it is of advantage when plural bases designed in the manner of posts are present. Such structure enables plural artificial teeth and/or crowns or beam-shaped intermediate parts to be received which, in the form of cross-beams bearing on the bases, interconnect all bases so as to improve the mounting and, resp., connection of the prosthesis to the implant and/or to increase the strength of the junction or joint between the prosthesis and the implant.

Another possible advantageous embodiment provides all longitudinal axes of the bases to extend transversely or diagonally to the longitudinal extension direction of the support structure. This allows for aligning each of the bases for each patient individually adapted to the optimum positioning of the prosthesis.

It is also advantageous when all of the longitudinal axes of the bases point exactly to the same spatial direction. In this way, the bases can be interconnected more easily by a cross-beam, for example, so as to enlarge the bearing surface of the prosthesis and/or to improve the stability of the seat of the prosthesis.

Another possible aspect of the invention provides that the support structure is grid-shaped or has one or more grid portion(s) and/or perforated lands. On the one hand, material and thus also costs can be saved and, at the same time, growing of bone and/or soft tissue into the grid structure can be promoted, which results in a stable connection by formation of a tertiary stability between the implant and the bone surrounding the implant.

It is of advantage in this context that the support structure, the grid portion and/or the land include(s) one perforation or more perforations in the form of a through-hole such as a bore. Thus, the grid structure at the same time may be used as a securing device and consequently separately provided securing points/devices can be dispensed with.

It is of advantage that the through-hole is designed to receive a screw to be screwed into the bone. Thus, the arrangement of separate through-holes on the implant for receiving screws can be dispensed with.

Moreover, it is advantageous to separate or space the distal part from a truncated cylinder portion via a tapered area, as in this way already very small heights between the dental implant and the prosthesis resting thereon can be realized, because no minimum lengths such as a minimum thread depth have to be observed.

It is also advantageous when the base includes a cylindrical outer contour or a flux-optimized outer contour. This helps to avoid fatigue symptoms of the implant material due to a design of the base which is not flux-optimized.

An advantageous embodiment provides that the base has an at least partial hollow-cylindrical shape preferably on the distal side. This shape offers maximum variation for the configuration of the connection of the prosthesis.

The base or bases is/are advantageously inserted and/or positioned so as to replace bone material and, resp., can be positioned so as to replace bone material. In this way, complex bone reconstructions by the patient's own or foreign bone material can be avoided.

Another aspect provides that at an implant plural bone formfitting sections are provided and are geometrically configured and aligned so that a form-fitting seat on the bone is enforced, especially during insertion or in the inserted state in the animal or human body. This allows to unambiguously place the implant without any major effort and to dispense with any separate positioning aids.

It is of advantage when the bone formfitting sections are geometrically configured and aligned so that the seat enforces one single stable abutting position of the implant on the bone. Thus, positioning is facilitated and the risk of wrong positioning of the implant is significantly reduced or almost completely avoided.

An implant on which at least three spatially separated bone formfitting sections are present has turned out to be advantageous. Plural spatially separated bone formfitting sections help to increase the abutting and positioning accuracy of the implant.

It is of further advantage when each bone formfitting section is prepared in a different spatial direction at a different bone portion for abutting on each other. Thus, the abutting and positioning accuracy of the implant is further increased and the positional stability of the implant is enhanced. This means that the implant is largely prevented from shifting in its position.

Moreover, the preparation of the bone formfitting section is advantageous so that a bone portion can be surrounded. Surrounding of a bone portion helps to further reduce the risk of shifting of the implant.

One advantageous embodiment provides that the bone formfitting section is formed by the support structure or a component separate therefrom, preferably in a single piece, integrally and/or from a single material. The single-part design of the bone formfitting section and the support structure helps to reduce the number of parts and to save material costs. Moreover, the single-piece design also helps to increase the positioning accuracy of the support structure and/or of the separate component.

The patient-specific tailored design of the bone formfitting section and/or of the support structure as a solid component such as a rod and/or by an individual bone and the use of CAD/CAM with respect to said outer contour close or adjacent to the bone, has turned out to be advantageous. In this manner, an implant individually adapted to the needs of each patient can be produced.

It is moreover advantageous that in the bone formfitting section at least one screw seating hole or plural screw seating holes is/are present. Thus, the bone formfitting sections at the same time serve as a boring template and as a securing device for securing the implant to the bone.

Another advantageous embodiment shows that the bone formfitting section and/or the support structure includes one or more coupling area(s) so as to secure the bone formfitting section to the support structure.

Moreover, the presence of multiple grid fastening points has turned out to be of advantage. Thus, the securing of the implant to the bone can be individually adapted to the patient and nerve paths as well as possibly existing teeth can be avoided during securing.

Further advantageous is an implant in which securing areas are predefined and geometrically prepared on the support structure for receiving one or more screws to be screwed into the bone, with one or more bases for receiving a prosthesis being present at a spatial distance thereof. Thus, the support structure serves both as boring and positioning template. In addition, the spatial separation of the mounting of the implant on the bone (first screwing axis) from the mounting of the prosthesis (second screwing axis) prevents premature fatigue symptoms of the implant material due to excessive mechanical stress at one spot.

In this context it is advantageous when a longitudinal axis through the screw to be inserted or being inserted is aligned transversely, diagonally or skew relative to a longitudinal axis of the base, especially relative to a screwing axis of the base. In this way, the direction of the screw being inserted or to be inserted can be set in a flux-optimized manner according to possibly present influencing factors such as nerve paths or teeth, and, moreover, the already afore-described local mechanical overload of the implant can be avoided.

Another advantageous embodiment provides that the securing area is distanced from the base by more than the length of a screw and/or more than 1.2, 2 or 3 times the thickness in the securing area and less than 500 times the length of a screw and/or less than 400 times the thickness in the securing area. Thus, the required strength of the implant can be ensured and premature fatigue symptoms can be avoided.

It has turned out to be advantageous when the base is configured so that it enables connection of a prosthesis or an intermediate part according to the locking or non-locking principle.

Furthermore, it is of advantage when the implant, for example the support structure and/or the base or any one of the bases, is in the form of a reservoir for a medical drug or a pharmacological drug. Thus, it is possible to place e.g. drugs, especially those which have to be administered/taken over a quite long period, there in the form of a drug-release system such as a drug-release capsule, and to administer them in this way. This is advantageous especially for patients who permanently have to take medical or pharmacological drugs, as such intake can no longer be forgotten and overdosing can be avoided.

A further advantage is constituted by preparing the implant for converting chewing energy and preferably for charging accumulators. The energy produced in this way can be used to supply energy to smaller accumulators present in the body, for example.

Another advantageous embodiment provides the implant to be in the form of a jaw implant, such as a mandibular or maxillary implant. Such implant can be applied to partially toothed as well as toothless jaws.

Moreover, it is of advantage when the support structure is designed/prepared in terms of material and geometry so as to enable a telescoping arrangement of the prosthesis. Thus, also states of major bone defects, such as e.g. after tumor operations including the resection of parts of the jaw, can be treated.

It is also advantageous when the support structure and/or the base is/are provided with a coating which promotes bony growth, strengthens the immunologic system, causes an antibiotic effect and/or assumes a reservoir function, for example using bone morphogenetic proteins (BMPs).

In addition, it is of advantage when one component or all components is/are made from titanium, a titanium alloy or a Ti—Al alloy. Titanium and titanium alloys have high biocompatibility and high inertia and therefore constitute a material suited for an implant.

Another advantageous embodiment provides a positioning aid being present on the support structure and/or the base. Said positioning aid assists the operating surgeon during insertion of the implant in checking the correct positioning and subsequently during follow-up in checking whether the implant might have shifted.

In this context, it is advantageous when the positioning aid is a marker, such as a laser marker and/or prominence, e.g. a bead. The prominence is of advantage especially for later checking by means of X-ray, as said prominence is evident from such pictures.

The design of the support structure as a resecting, positioning and/or boring template is advantageous. By integrating said functions in the implant and, resp., the support structure, additional means which usually serve as such templates can be dispensed with.

It is of further advantage when the coupling area or the coupling areas include(s) a hole partially or completely penetrating the same, e.g. in the form of a bore, preferably for receiving a screw.

Furthermore, a method for producing an implant, comprising the step of capturing individual patient data, including e.g. the bone and/or soft-tissue configuration, including the respective outer contour, e.g. using MRT or CT, creating the support structure and/or the base on the basis of the individual patient data, e.g. by CAD/CAM techniques, preferably making use of laser-sintering, is of advantage.

Moreover, a method for implanting an implant produced as described above into an animal or human body is described.

In other words, the invention consists in the fact that an implant is made available which can be unambiguously positioned on the bone due to at least two bone formfitting sections and whose screw holes are configured so that they serve as a forced guide for a drill used to introduce the holes into the bone, which means that the implant with the screw holes simultaneously serves as a boring template. Furthermore, the invention comprises a method for producing said implant.

Hereinafter the invention shall be illustrated in detail by means of drawings showing different variations, wherein.

The figures are merely schematic and only serve for the comprehension of the invention. Like elements are provided with like reference numerals. Features of the individual embodiments may as well be realized in other embodiments. Hence, they are interchangeable.

Figure 1:
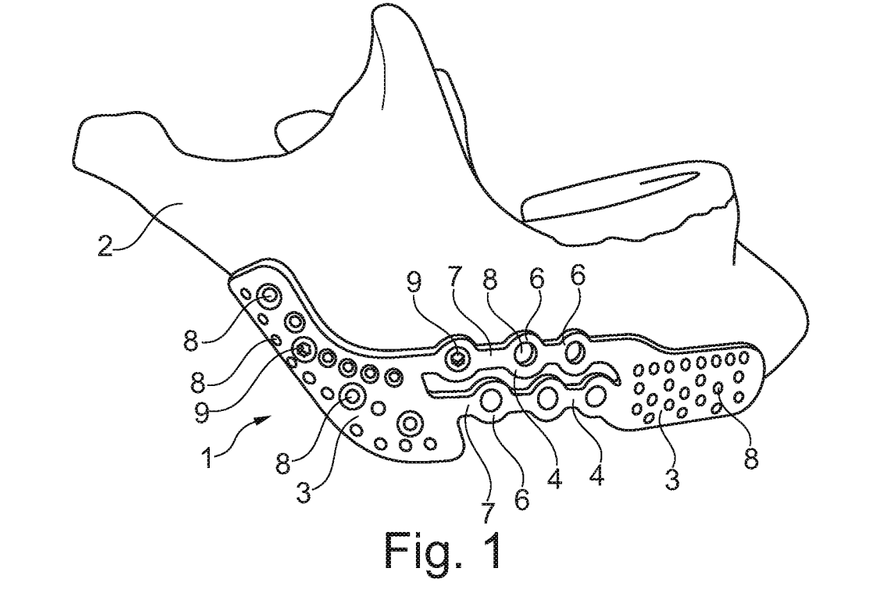
FIG. 1 shows a side view of the implant on a jaw bone in a first embodiment.

FIG. 1 illustrates a side view of the implant 1 in a first embodiment. The implant 1 in this embodiment serves as a mandible implant which abuts on a bone 2 of the mandible. The implant 1 has bone contour sections 4 as well as bone support surfaces/bone formfitting sections 3. The bone formfitting sections 3 serve for surrounding the bone 2, thus the position of the implant 1 being definitely secured (cf. also FIG. 2).

The bone contour sections 4 and the bone formfitting sections 3 as shown in FIG. 1 together form a support structure 5 of the implant 1, with the bone formfitting sections 3 being more solid than the bone contour sections 4. The bone contour sections 4 in this embodiment are grid-shaped and have annular sections 6 which are connected to each other and to the bone formfitting sections 3 via lands 7. The annular sections 6 serve as screw seating holes 8.

The bone formfitting sections 3 include plural screw seating holes 8 having different inner diameters. At the proximal bone formfitting section 3 (on the left in this figure) as well as at the medial bone contour section 4 screws 9 are exemplified which serve for securing the implant 1 to the bone 2. Said screws 9 may be e.g. osteosynthesis screws.

Figure 2:
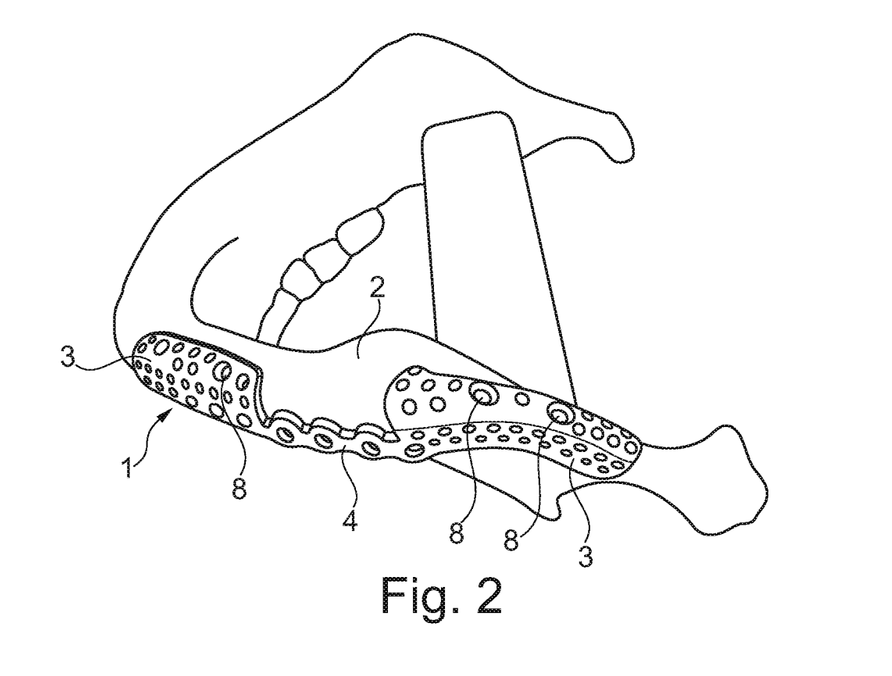
FIG. 2 shows a bottom view of the implant mounted on the jaw bone from FIG. 1.

FIG. 2 illustrates a bottom view of the implant 1 according to the first embodiment. It is especially clear from this figure that the bone formfitting sections 3 surround e.g. the full surface of the bone 2, whereas the bone contour sections 4 abut on the surface of the bone 2 and quasi follow the bone contour. By the bone formfitting section 3 surrounding the bone 2 the position of the implant on the bone 2 is unambiguously secured, whereas, when a conventional implant which exclusively has bone contour sections 4 is applied, said implant cannot be unambiguously and permanently positioned relative to the bone.

From this figure the screw holes 8 provided with different inner diameters are equally clearly evident. Of course, also equal inner diameters are possible. It is noted in this context that each screw hole 8 is prepared for receiving a screw 9 (cf. FIG. 1), but only selected holes are used for securing the implant 1 to the bone 2.

Figure 3:
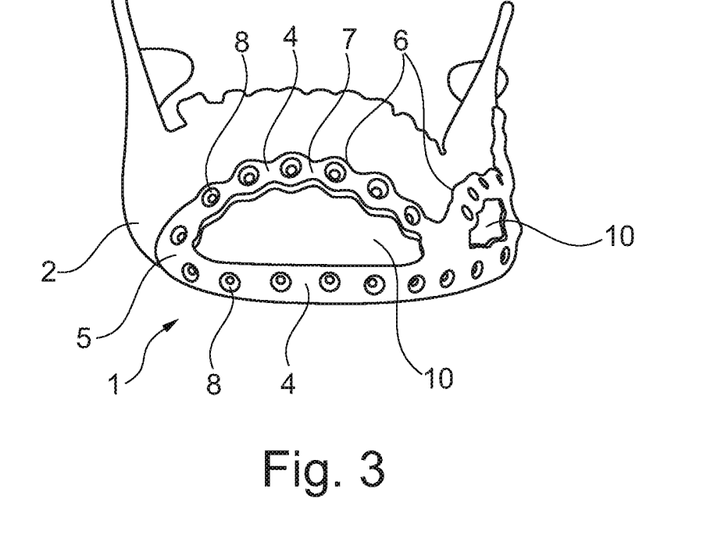
FIG. 3 shows a front view of a second embodiment of an implant mounted on a jaw bone.

FIG. 3 illustrates a front view of the implant 1 in a second embodiment. In this embodiment, the implant 1 encompasses/surrounds the bone 2 of a mandible on one side (on the right in this figure) and in the chin region. In this embodiment, the support structure 5 is predominantly grid-shaped consisting of annular portions 6 and lands 7. Since sufficient stability can be obtained already by such grid-shaped support structure 5, recesses 10 can be provided for saving material.

Said second embodiment of the implant 1 clearly shows the design of the bone contour sections 4 following the bone outer contour and of the bone formfitting sections 3 (cf. FIG. 4), wherein the bone formfitting sections 3 abut on plural areas of a bone 2. This means that a bone formfitting section 3 is formed quasi of at least two interconnected bone contour sections 4 which are not aligned in parallel to each other. Preferably, said bone contour sections 4 are formed of a single piece and a single material.

Figure 4:
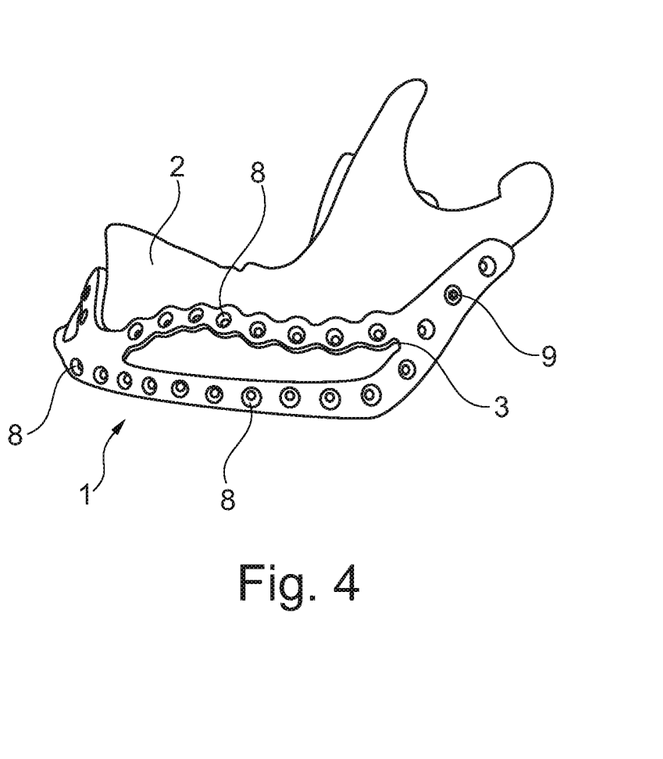
FIG. 4 shows a side view of the implant from FIG. 2.

FIG. 4 illustrates a side view from laterally, i.e. in the representation from the right, of the implant 1 of the second embodiment shown in FIG. 3. In this figure, the bone formfitting section 3 at the rear area of the bone 2 is clearly evident (on the right in FIG. 4). This embodiment of the implant 1 equally includes annular portions 6 which serve as screw seating holes 8 and are prepared for receiving screws 9.

It is evident that in this embodiment of the implant 1 the screw seating holes are positioned diagonally or skew relative to each other and thus forcedly predetermine for the drill different directions for introducing holes into the bone 2. Moreover, in this embodiment the screw seating holes 8 are equally provided with different inner diameters.

Figure 5:
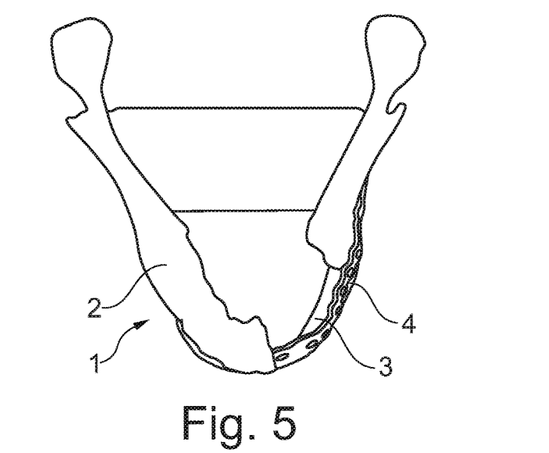
FIG. 5 shows a top view of a third embodiment of an implant mounted on a jaw bone.

FIG. 5 illustrates a top view onto the implant 1 in a third embodiment. Said third embodiment resembles the aforedescribed second embodiment of the implant 1 (cf. also FIG. 6 and FIG. 7) but, in addition to the bone formfitting section 3 at the rear area of the bone 2, also includes a bone formfitting section 3 at the lateral area of the bone 2.

In said third embodiment, the implant 1 serves e.g. for bridging jaw bone defects and for stabilizing the still existing jaw bone 2. Moreover, in the area of the bone defect it serves as a basis for introducing a foreign bone segment or an artificial bone (both of which are not represented) so as to compensate for the defect.

Figure 6:
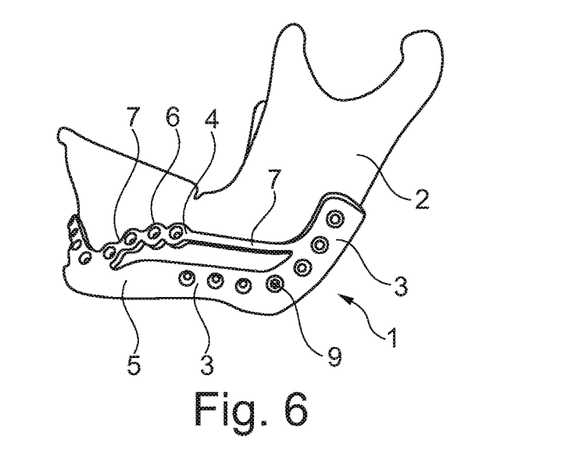
FIG. 6 shows a side view of the implant from FIG. 3.

FIG. 6 shows a side view of the implant 1 from the right while being based on FIG. 5. It is evident that the support structure 5 is configured to be more solid in the area of the bone formfitting sections 3 than in the area of the bone contour sections 4 which have a grid-shaped structure.

Figure 7:
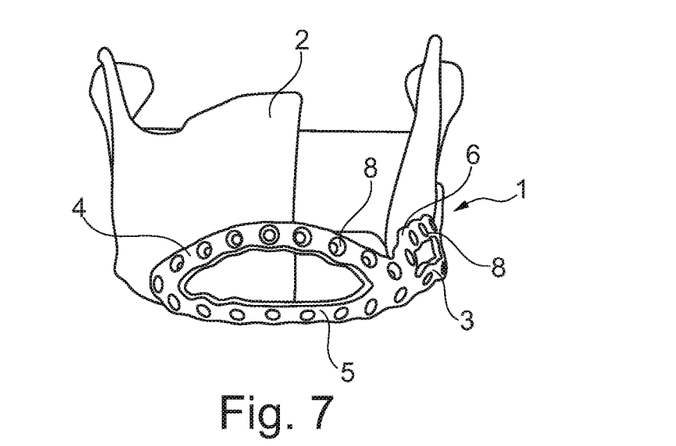
FIG. 7 shows a front view of the implant from FIGS. 3 and 4.

FIG. 7 shows a front view of the implant 1 in the third embodiment. From this figure just as from FIG. 5, it is evident that the implant 1 has an individually formed contour in the area of the bone defect. When designing said contour, it is designed by way of a jaw bone 2 which is intact in the model so as to be able to position the foreign bone (not shown) inserted later in a precise and exact manner corresponding to the original jaw bone contour. This prevents any plastic changes of contour from externally occurring due to the bone replacement introduced to the defect, and further enables a dental prosthesis possibly applied thereto to be aligned corresponding to the existing dentition structure.

Hence, flux-optimized alignment or, resp., positioning of the implant required for the dental prosthesis is possible, which allows the load of such dental implant as well as of the implant according to the invention to be minimized. In this way, fatigue symptoms of the implant material will occur more rarely or at least later and the risk of the implant getting loose can be significantly reduced.

Figure 8:
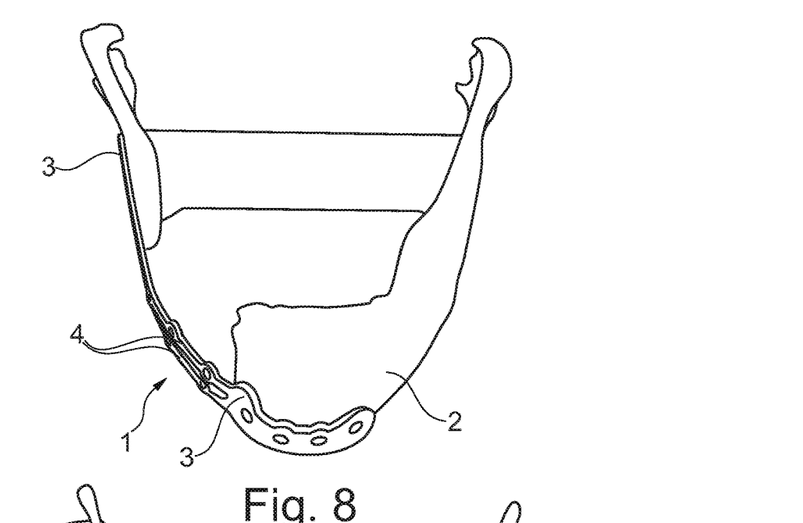
FIG. 8 shows a top view of a fourth embodiment of an implant mounted on a jaw bone.

FIG. 8 shows a top view of the implant 1 in a fourth embodiment. In this embodiment, in the area of the defect of the bone 2 there is provided no bone formfitting section 3 but merely bone contour sections 4 which exactly position the later introduced foreign bone by means of their contour. In the area of the chin as well as in the rear area of the bone 2 (cf. FIG. 10) bone formfitting sections 3 are provided.

The bone contour sections 4 are grid-shaped and consist of a linear arrangement of annular portions 6 and lands 7 in a respective alternating manner.

Figure 9:
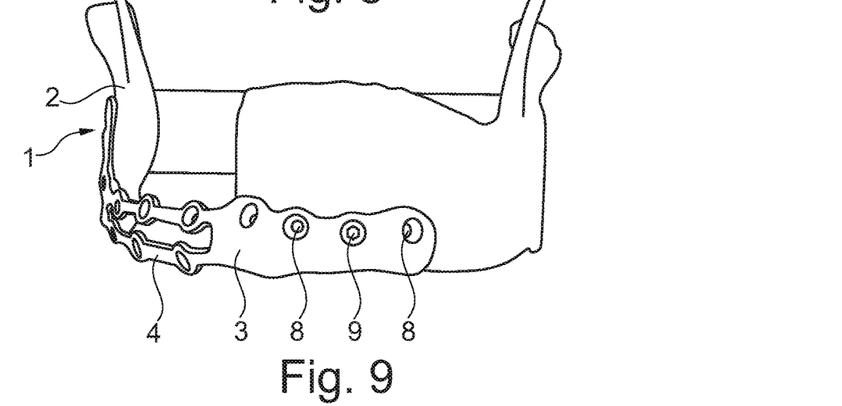
FIG. 9 shows a front view of the implant from FIG. 8.

FIG. 9 illustrates a front view of the implant 1 in the fourth embodiment. In this case, the more solid configuration of the bone formfitting section 3 in the area of the chin is clearly visible. Plural screw seating holes 8 which serve for receiving screws 9 are provided at said bone formfitting section 3. Via the alignment of a screw seating hole 8 the bore vector for the holes to be introduced to the bone 2, and thus the position of the screw 9 in the bone 2, is defined and/or forcedly predetermined.

Figure 10:
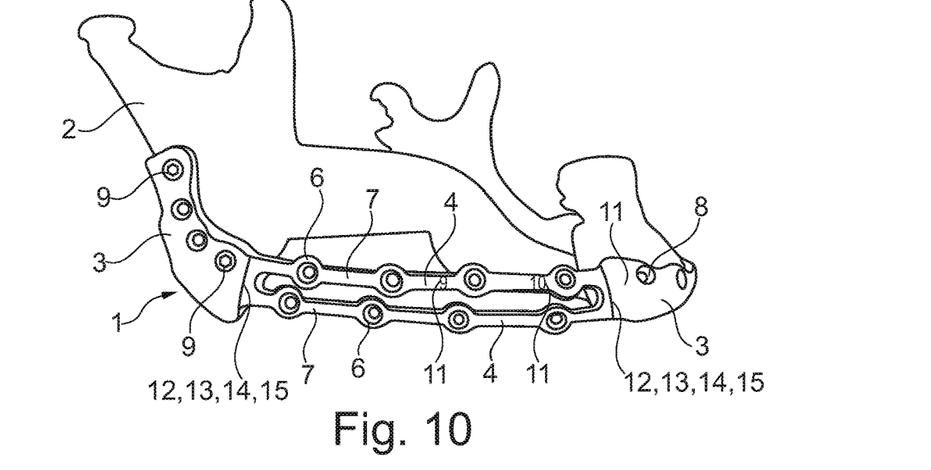
FIG. 10 shows a side view of the implant from FIGS. 8 and 9.

FIG. 10 illustrates a side view of the implant 1 in the fourth embodiment. This figure reveals that also the bone formfitting section 3 at the rear area of the bone 2 is designed to be more solid than the bone contour sections 4 which interconnect the two bone formfitting sections 3.

The implant 1 in this embodiment has a numbering 11 of the screw seating holes 8 as well as two markers 12 which are provided at each of the left and right ends of the bone contour sections 4.

The numbering 11 of the screw seating holes 8 serves as an orientation guide for the operating surgeon, as not all screw seating holes 8 are used for securing the implant 1 to the bone 2 by means of screws 9. The numbering 11 assists the operating surgeon in reproducing during the surgical intervention into which of the screw seating holes 8 screws 9 are to be set and he/she can check whether he/she has set all necessary screws 9.

The markers 12 are laser markers 13 and/or prominences 14 which can be detected by means of a probe (not shown). The markers may as well be such that they are detectable by CT data collection and/or an X-ray picture. Such markers 12 assist the operating surgeon, on the one hand, in checking the correct positioning of the implant 1. On the other hand, said markers 12 may be used to mark the area in which the bone 2 has to be resected (e.g. by reason of existing tumor tissue) and thus during surgical intervention serve as check markers 15 which the operating surgeon may scan with the aid of a probe and/or may detect optically/haptically and so that he/she may check whether he/she has completely resected the bone area to be removed.

LIST OF REFERENCE NUMERALS

1 implant
2 bone
3 bone formfitting section
4 bone contour section
5 support structure
6 annular portion
7 land
8 screw seating hole
9 screw
10 recess
11 numbering
12 marker
13 laser marker
14 prominence
15 check marker

The invention claimed is:

1. An implant for attaching to a bone, the implant comprising:
  bone formfitting sections which are inclined relative to each other and configured to rest on a surface of the bone, wherein two bone formfitting sections are aligned relative to each other in a sub-region of the implant inserted in its original shape so as to secure a position of the implant configured to abut on the bone in three spatial directions;
  screw seating holes aligned such that they can be used as a boring template for introducing bores into the bone; and
  a support structure integrally formed with the bone formfitting sections, wherein the support structure includes a marker configured to serve as a positioning aid to position the implant on the bone.

2. The implant for attaching to a bone according to claim 1, wherein the screw seating holes are aligned diagonally or skew relative to each other.

3. The implant for attaching to a bone according to claim 1, wherein an inner diameter of one of the screw seating holes is adjusted to an outer diameter of a drill and/or of an intended hole in the bone.

4. The implant for attaching to a bone according to claim 3, wherein an inner diameter of at least one of the screw seating holes amounts to 0.8, 0.85 or 0.9 to 0.99 times an intended bone hole.

5. The implant for attaching to a bone according to claim 1, wherein at least one of the screw seating holes is arranged in an area of the support structure of the implant.

6. The implant for attaching to a bone according to claim 5, wherein the screw seating holes are formed to be inclined and/or diagonal relative to a surface of the support structure.

7. The implant for attaching to a bone according to claim 1, wherein the implant is in a form of a boring template comprising drill guide bushes.

8. A method for producing an implant according to claim 1, the method comprising:
- capturing a patient-specific bone structure by MRT and/or CT;
- creating a CAD model of the patient-specific bone structure;
- creating a CAD model of an individually shaped implant based on the CAD model of the patient-specific bone structure; and
- producing the individually shaped implant based on the CAD model.

9. The method for producing an implant according to claim 8, wherein, based on previously obtained patient-specific data, the screw seating holes are introduced such that after implanting the implant the screw seating holes can be used as a forced guide for a drill which can be employed for introducing holes into the bone.

* * * * *